United States Patent [19]

Troutner et al.

[11] 4,091,880
[45] May 30, 1978

[54] SURGICAL WIRE INSERTER APPARATUS

[75] Inventors: Vernon H. Troutner, South St. Petersburg; Carl L. Foltz, Holiday; Arthur F. Trott, Largo, all of Fla.

[73] Assignee: Concept Inc., Clearwater, Fla.

[21] Appl. No.: 688,574

[22] Filed: May 21, 1976

Related U.S. Application Data

[63] Continuation-in-part of Ser. No. 623,391, Oct. 17, 1975, Pat. No. 4,050,528, which is a continuation-in-part of Ser. No. 610,869, Sep. 5, 1975.

[51] Int. Cl.$^2$ .............................................. A61B 17/16
[52] U.S. Cl. .............................. 173/163; 128/92 EB; 173/170; 279/51
[58] Field of Search ............... 128/92 EC, 92 EB; 32/27; 279/51, 53; 173/163, 169, 170; 310/50

[56] References Cited

U.S. PATENT DOCUMENTS

| | | | |
|---|---|---|---|
| 2,297,174 | 9/1942 | Tabb et al. | 279/51 X |
| 2,448,423 | 8/1948 | Dodge | 279/51 |
| 3,109,238 | 11/1963 | Marks | 173/163 X |
| 3,325,899 | 6/1967 | Staunt | 279/53 X |
| 3,499,223 | 3/1970 | Lieb et al. | 279/53 |
| 3,509,629 | 5/1970 | Kidokoru | 32/27 |
| 3,724,563 | 4/1973 | Wickham et al. | 173/163 |
| 3,813,782 | 6/1974 | Nilles | 279/53 X |
| 3,883,789 | 5/1975 | Achenbach | 310/50 X |

Primary Examiner—Ernest R. Purser
Assistant Examiner—William F. Pate, III
Attorney, Agent, or Firm—Gipple & Hale

[57] ABSTRACT

A portable surgical wire inserting instrument comprising a housing defining a handle and a head casing. The housing handle holds a removable power pack in which is mounted a motor and a source of power electrically connected to the motor. A miter gear extends from the power pack and is connected by a drive shaft to the motor. A collet is mounted in the housing and is selectively adjusted to grip a plurality of different diameter surgical wires through the action of a knob and cam mechanism located on top of the instrument head.

Rotation of the knob to one of a number of different positions establishes a number of different positions for the pivot points of thrust bars which act upon pins to draw the collet into an internally coned tube. Each position corresponds to a location of the thrust bar pivots suitable for gripping wires of different sizes. Gripping of the wire is accomplished by rotating a cam which moves the thrust bars rearward against pins which move a draw tube rearward and further draws the collet into the internally coned tube causing the jaws of the collet to squeeze in and grip the surgical wire. A miter gear on the coned tube connects with the miter gear extending from the power pack with the gears being adapted to rotate the coned tube upon energization of the motor.

11 Claims, 13 Drawing Figures

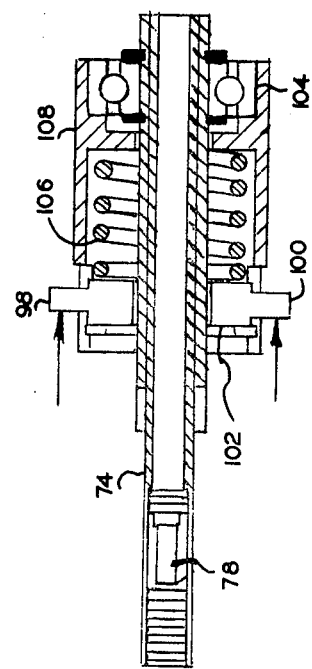
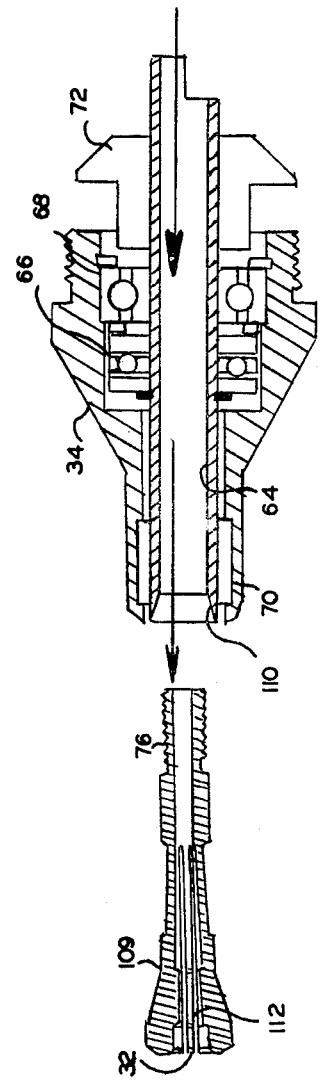
FIG. 4c
FIG. 4b
FIG. 4a

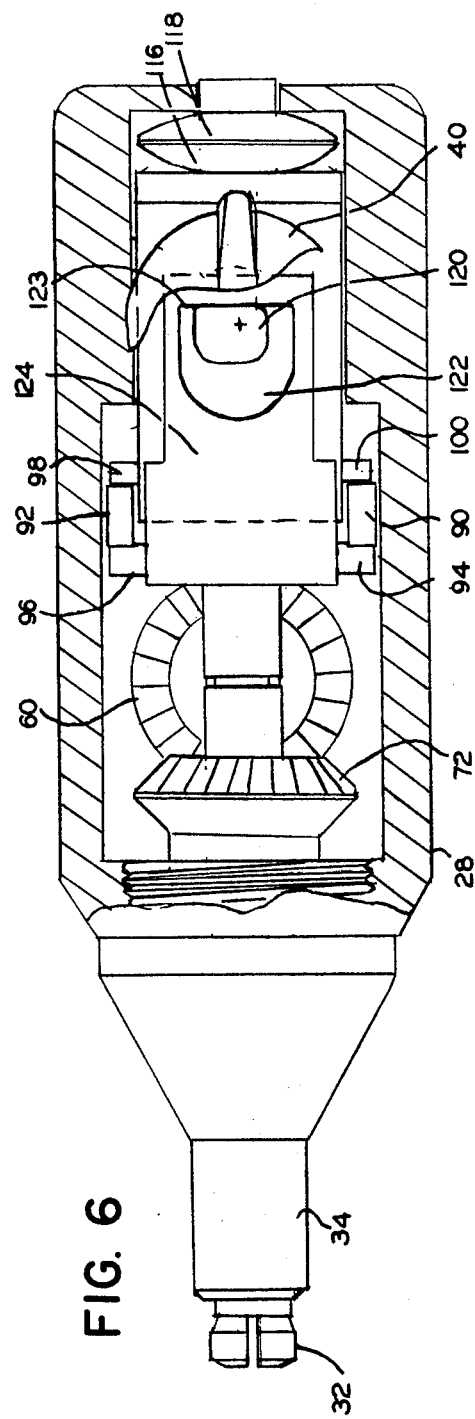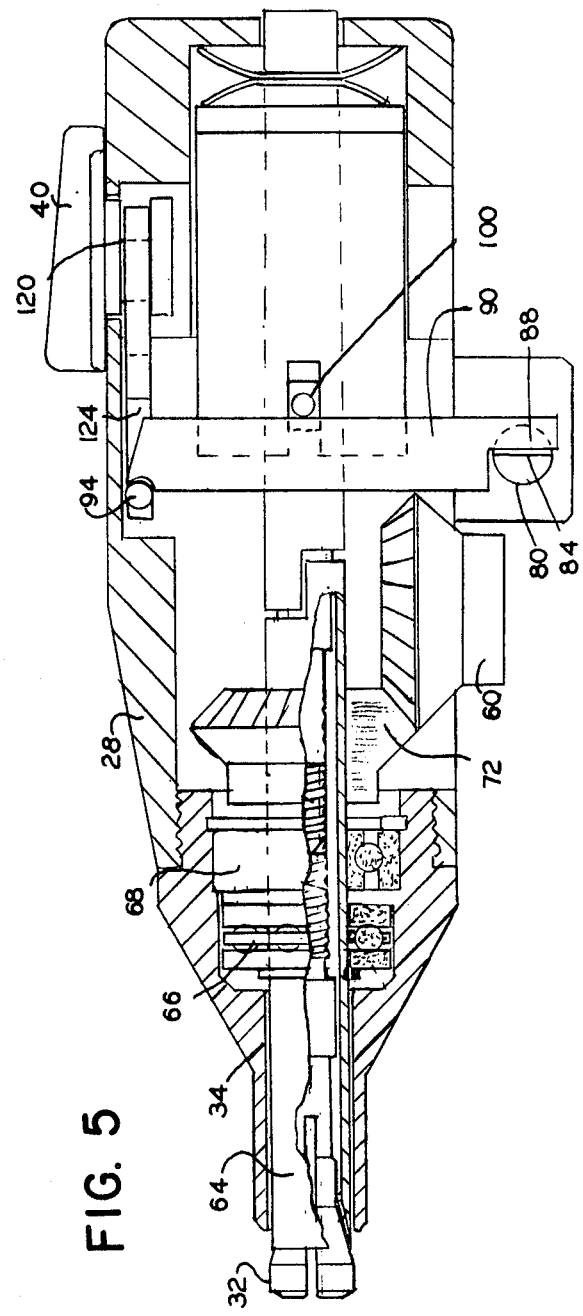

SURGICAL WIRE INSERTER APPARATUS

This is a continuation-in-part of U.S. patent application Ser. No. 623,391 filed Oct. 17, 1975 now U.S. Pat. No. 4,050,528 which is a continuation-in-part of U.S. patent application Ser. No. 610,869 filed Sept. 5, 1975.

BACKGROUND OF THE INVENTION

The present invention generally pertains to a surgical wire inserter adapted to insert a circular prosthetic device into or through bones to provide support and fixation while the bone structure is mending or to provide anchorage for traction but more particularly pertains to a rotary wire inserting device utilizing a surgical wire.

In the prior art a prosthetic wire device usually circular in cross section is generally inserted into the bone by means of a pre-drilled hole or more commonly by driving the wire with a suitable drill chuck and letting the wire bore its own hole by means of a spade or trocar tip. A trocar point is the point most commonly used on such wires. One such device which has been used to insert wires is a device called a Loth-Kirschner extension drill. The drill is hand operated with the drill bit being rotated by suitable gearing which is turned by a handle much like that of a fishing reel.

Another device which has been used is a pneumatic wire driver manufactured by the Stryker Corporation. This device is a hand held device with a trigger. An air supply, which is connected to the device by way of a hose, passes through the handle of the gun causing the wire to rotate so that it obtains a sufficient torque to be driven into the bone.

Generally speaking the prosthetic wires which are used in both of these instruments and wires which are used in the operating room are circular in cross-section ranging from 0.028 to 0.062 inches in diameter and are primarily provided with a ground spade point or a trocar point.

Because of the circular cross section and small diameter of these wires they are difficult to hold in a collet tightly enough to prevent slipping during installation.

SUMMARY OF THE INVENTION

The present invention incorporates a wire having anti-rotational features which eliminate the slippage of the wire in the drill collet during installation. The novel instrument which is used to rotate the wire contains a removable power pack carrying a motor and battery power source adapted to rotate the wire. The wire inserter instrument is designed to utilize a prosthetic wire of a substantially circular cross section having one or more flats to provide anti-rotational keying with the collet which is used for installation.

A portable surgical wire inserting instrument is disclosed comprising a housing defining a handle and head casing. The housing handle holds a removable power pack in which is mounted a motor and a source of power electrically connected to the motor. A miter gear extends from the power pack and is connected by a drive shaft to the motor. A collet is mounted in the housing and is selectively adjusted to grip a plurality of different diameter surgical wires through the action of a knob and cam mechanism located on top of the instrument head.

Rotation of the knob to one of a number of different positions establishes a number of different positions for the pivot points of thrust bars which act upon pins to draw the collet into an internally coned tube. Each position corresponds to a location of the thrust bar pivots suitable for gripping wires of different sizes. Gripping of the wire is accomplished by rotating a cam which moves the thrust bars rearward against pins which move a draw tube rearward and further draws the collet into the internally coned tube, causing the jaws of the collet to squeeze in and grip the surgical wire. A miter gear on the coned tube connects with the miter gear extending from the power pack with the gears being adapted to rotate the coned tube upon energization of the motor.

Although the invention will be set forth in the claims, the invention itself and the manner in which it may be made and used, may be better understood by referring to the following description taken in connection with the accompanying drawings forming a part thereof in which like reference numerals refer to like parts throughout the several views and in which:

BRIEF DESCRIPTION OF THE DRAWINGS

FIGS. 4a, 4b and 4c together represent an exploded sectional view of the split spring collet, collet tube and nose sub-assembly, draw tube and spring cartridge sub-assembly of the wire gripping mechanism of the wire inserter instrument;

FIG. 5 is a side elevational view partially cut away and partially in section of the instrument head;

FIG. 6 is a top plan view partially in section and partially cut away of the instrument head;

DETAILED DESCRIPTION OF THE DRAWINGS

Figure 1:
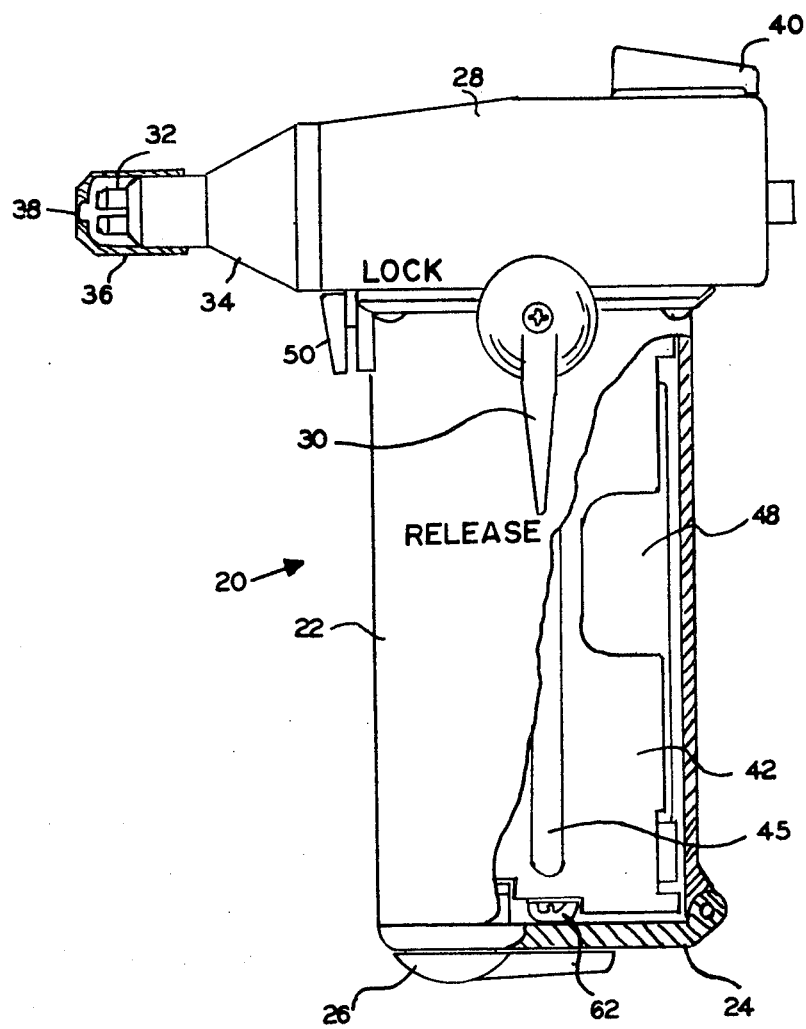
FIG. 1 is a side elevational view partially in section of the wire inserter instrument.
Figure 2:
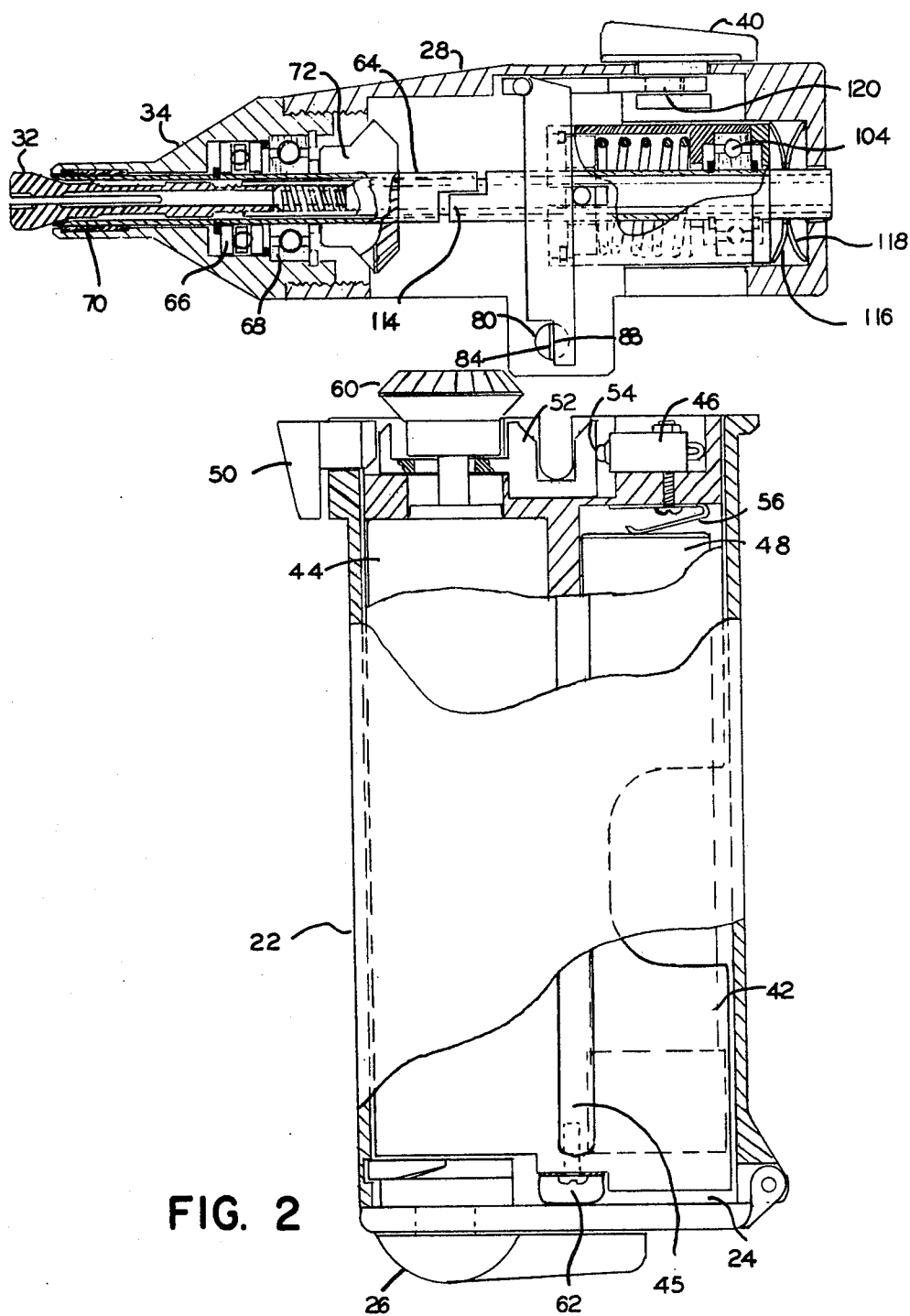
FIG. 2 is a side elevational view partially exploded and partially in section of the wire inserter instrument.
Figure 3:
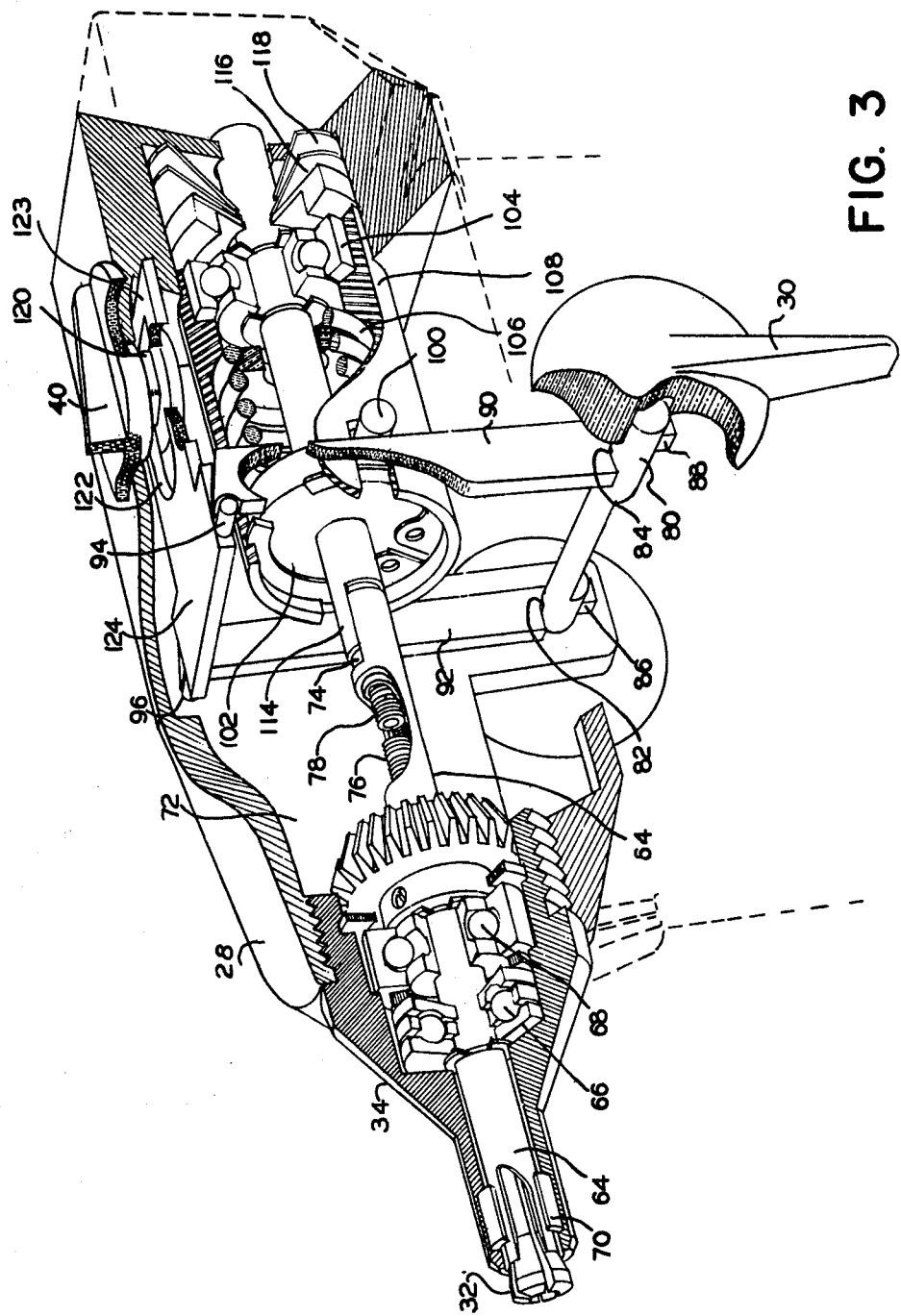
FIG. 3 is a perspective view of the instrument head of the wire inserter instrument partially cut away.
Figure 7:
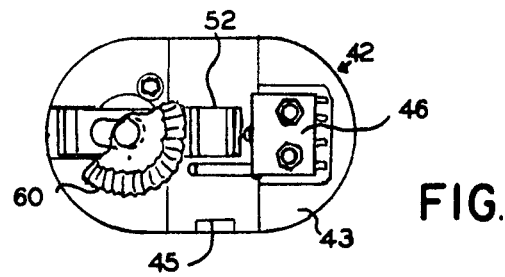
FIG. 7 is a top plan view of the removable power pack of the instrument showing the miter gear partially cut away.
Figure 8:
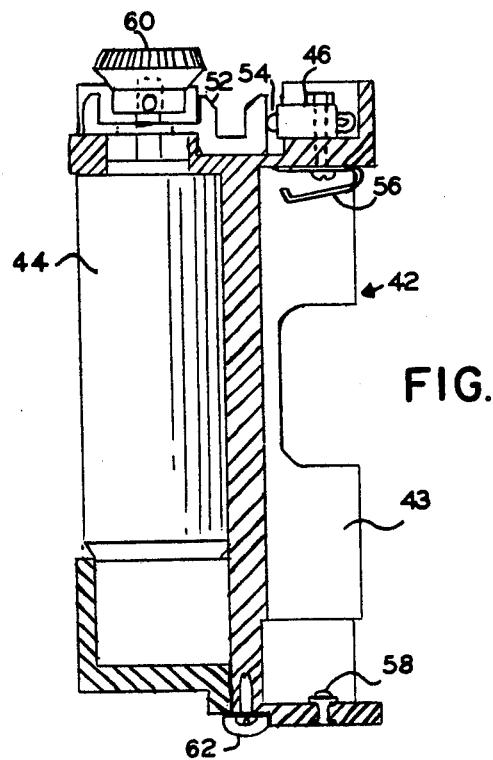
FIG. 8 is a side elevational view partially in section of the removable power pack of the instrument.
Figure 9:
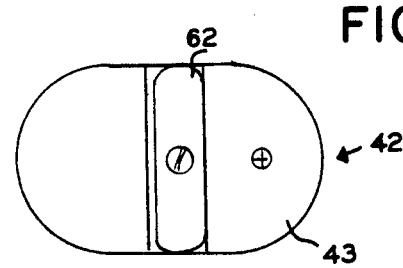
FIG. 9 is a bottom plan view of the removable power pack of the instrument.

The present invention as shown in FIGS. 1–11 concerns a unique surgical wire inserter apparatus which utilizes a surgical wire.

The wire which is used in the assembly preferably is formed with four flats formed as chords each subtending a center angle of 45° located in an equal spaced manner around the circumference.

The wire inserter instrument 20 as shown in the figures comprises a handle and a head assembly with a removable power pack. The handle 22 is hollow with a hinged cover 24 which is held closed by a lever operated latch 26. Mounted on the handle is an instrument head assembly 28 which contains the mechanism for gripping a surgical wire 21. A knob 40 on the top of the instrument head is used to initially adjust the instrument for gripping different diameters of surgical wire as will be more fully described later on in the specification.

When a surgical wire is placed within the head assembly after it has been adjusted to receive the wire, the mechanism is activated by moving a side lever 30 from the "RELEASE" position to the "LOCK" position as is shown in FIG. 1. The lever movement causes a split collet 32 in the nose 34 to retract and squeeze closed gripping the surgical wire 21 inserted into the collet.

A disposable soft plastic collet cap 36 is pressed onto the nose portion 34 of the head assembly. The cap 36 is formed with a thin membrane 38 which when punctured by the surgical wire 21 forms a light wiping seal on the surgical wire to keep foreign material out of the head assembly 28.

Contained within the hollow handle 22 is a removable power pack 42 comprising a support or frame member 43, an electric motor 44 and associated gearing, a switch 46 and associated cross bar 52, and a rechargeable battery 48. When the trigger 50 which is mounted on the handle is pressed, the cross-bar 52 which is slidably mounted in the frame member 43 depresses button 54 on the switch 46 which completes an electrical circuit between the battery and the motor emergizing the motor. The motor turns a drive shaft and associated gearing rotating the collet and the surgical wire it is gripping. The rechargable battery 48 is retained in a cavity of the power pack frame and is connected electrically by two contacts 56 and 58 to the switch and motor. When the motor 44 is energized by the switch 46 a miter gear 60 is caused to rotate which drives the collet mechanism as will be later described. The removable power pack 42 is held in the handle with the latched cover 24 which bears against a leaf spring 62 on the power pack. The power pack frame member 43 is provided with a guide slot 45 which serves to fit over a projection (not shown) in the interior of the handle so that the power pack is always mounted into the handle in the correct position.

A collet tube 64 is mounted in the nose 34 by a thrust bearing 66 and a radial bearing 68 and is additionally supported by a Nylon bushing 70. A miter gear 72 is mounted on the collet tube and positioned to engage the miter gear 60 of the power pack so that the collet tube is driven to rotate when the motor is energized. As shown in FIG. 4, a draw tube 74 extends through the collet tube and engages the threaded portion 76 of the split spring collet 32. A hollow set-screw 78 is adjustably mounted in the threaded bore of the draw tube 74 to lock the collet 32 into a properly adjusted position. The end of the set screw is provided with a hexagonal configuration so that an allen wrench can be inserted into the interior of the draw tube to selectively position the set screw within the draw tube.

Rotation of the side lever 30 to the "LOCK" position rotates the cam rod 80. Flats 82 and 84 on the cam rod rotate against mating flats 86 and 88 on thrust bars 90 and 92. The thrust bars are pivoted at their other end on pins 94 and 96. Rotation of the cam rod causes the thrust bars to move rearward (away from the nose) against pins 98 and 100 extending from thrust washer 102. Pressure from the thrust bars onto these pins is transmitted to a ball bearing assembly 104 which is connected to the draw tube 74. Pressure from the pins is transmitted to the bearing assembly 104 through a spring 106 contained within cartridge 108. The spring serves to limit the pressure which can be applied to the bearings and collet.

When the cam rod 80 is rotated to "LOCK" position, the bearing 104 is moved rearward, moving the draw tube rearward, which pulls the conical surfaces 109 of the split collet into the mating conical inside surface 110 of the collet tube, causing the jaws 112 of the split collet to squeeze closed gripping the surgical wire. The collet jaws 112 which engage the surgical wire are flat to correspond with lengthwise flats on the surgical wire which prevents rotation and slipping of the wire in the collet. A spline arrangement 114 causes the draw tube 74 and collet 32 to rotate with the collet tube 64 when the motor is energized. Crescent springs 116 and 118 cause the draw tube and collet to be returned to the forward position when the cam rod is returned to the "RELEASE" position.

The wire size adjustment knob 40 on the instrument head is connected to a four faced cam 120 which engages a dee hole 122 in draw bar 124 which carries the pivot pins 94 and 96. Thus, when the knob 40 is rotated to the four positions in which the four cam faces of the cam 120 engage the flat surface 123 defining the dee hole 122 in the draw bar 124, the upper pivots 94 and 96 of the thrust bars 90 and 92 are adjusted selectively to one of four positions. As the flat surface of the dee hole 122 is moved rearward, the pivots 94 and 96 move rearward, forcing the thrust bars to move rearward, causing the draw tube to pull the collet into the collet tube. The engagement of the collet with the coned inner surface of the collet tube cause the collet jaws to close, so that varying sizes of smaller surgical wires can be gripped when the cam knob is rotated. Thus the four positions of the cam result in four adjustments of the instrument for gripping four sizes (diameters) of surgical wires which are preferably 0.028, 0.035, 0.045 and 0.062 inches. Additional micro adjustment of the instrument is accomplished by subsequently moving side lever 30 to the lock position as previously described.

Figure 10:
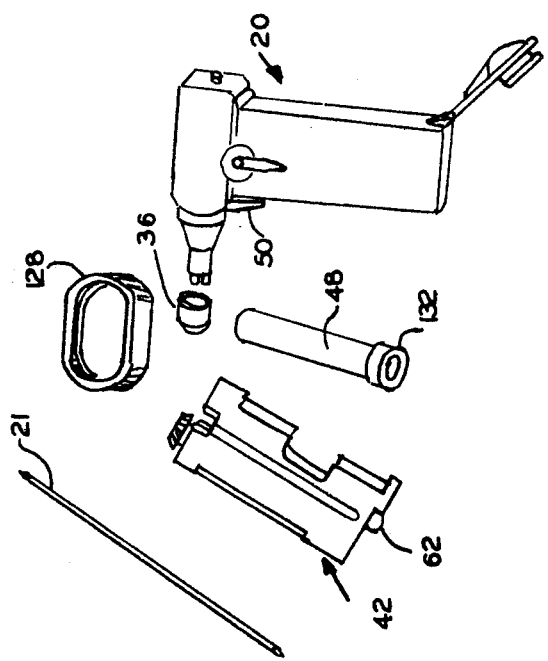
FIG. 10 is an exploded view of the wire inserter instrument, power pack, introducer funnel, battery, collet cap and surgical wire.

As shown in FIG. 10 the complete system consists of a surgical wire 21, the wire inserter instrument 20 with removable power pack 42 rechargeable battery 48 and disposable collet cap 36. A stepped introducer funnel 128 is used to cover the open end of the instrument handle so the non-sterile power pack can be installed into a sterile instrument without contaminating the outer surfaces of the instrument. The funnel is notched to allow installation of the funnel over the hinge cover.

Figure 11:
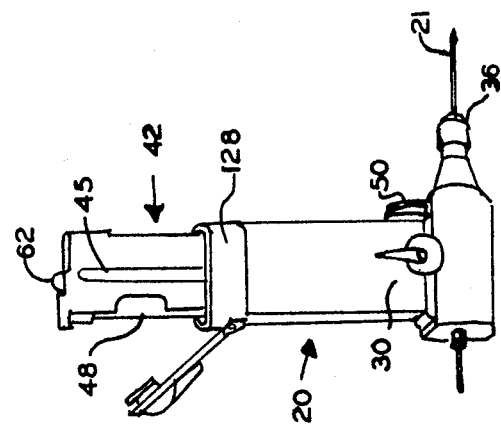
FIG. 11 is a view showing assembly of wire inserter instrument, power pack, introducer funnel, battery, collet cap and surgical wire.

FIG. 11 shows the power pack being installed into the instrument handle through the introducer funnel 128 with surgical wire 21 and collet cap 36 in place. A guard ring 132 on the positive end of the battery 48 assures the battery can only be installed in the proper direction of the power pack.

In operation, trigger 50 is pulled back towards the handle moving the cross bar 52. The button 54 of the micro switch 46 then energizes the motor 44.

It can thus be seen from the invention that the cover 24 can be released by turning latch 26 on the handle so that the power pack can be removed from the handle. The removal of the power pack allows either a battery to be placed in the power pack or allows the instrument 20 to be autoclaved for sterile use. Thus it can be seen that the instrument can be autoclaved in a conventional manner such as by heat and/or steam with no damage to the battery or to the motor. In addition, the power pack can be easily loaded into the handle without loss of instrument sterility through the use of the stepped funnel 128 as is shown in FIG. 11. As shown in FIG. 11 the instrument 20 is turned upside down with the cover 24 opened and the funnel mounted on the handle base over the hinge of the cover allowing the power pack to be dropped into the handle in an aligned position.

The funnel is preferably constructed of aluminum and the instrument housing and external parts are aluminum while the moving parts of the instrument are preferably constructed of stainless steel. However plastic or brass or other suitable material components can be used if such is desired.

While the preferred embodiment of the invention has been disclosed, it is understood that the invention is not limited to such an embodiment since it may be otherwise embodied in the scope of the appended claims.

What is claimed is:

1. A portable surgical wire inserting apparatus comprising a housing comprising a handle and a head assembly mounted to said handle; powering means completely enclosed yet removably mounted in said handle so that said powering means is not exposed to contamination from the outside environment during a surgical operation, said powering means comprising a body, motor means mounted in said body, a source of electrical power mounted in said body and electrically connected to said motor means; a wire holding tube means mounted in said head assembly, said wire holding tube means comprising a coned tube, a draw tube slidably mounted in said coned tube, a split collet member adjustably mounted in said draw tube and adapted to engage said coned tube so that the split sections of the split collet member are forced together to hold a wire placed therein, and draw tube moving means adapted to move said draw tube within said coned tube, said draw tube moving means comprising a first cam means mounted to said housing, said first cam means comprising a turning member, a cam member mounted to said turning member and adapted to be rotated by the movement of said turning member, a drive bar mounted in said head assembly, said drive bar defining a plurality of pivot points and an aperture into which said cam member is positioned, said cam member being positioned adjacent an aperture defining wall of the drive bar, said cam member being provided with a plurality of camming sides adapted to engage the aperture defining wall and drive the drive bar to one of a plurality of predetermined positions, the number of predetermined positions being equal in number to the number of camming sides, at least one thrust bar having one end pivotally mounted adjacent one of said drive bar pivot points and adapted to be moved by said drive bar, a thrust means mounted to said draw tube and positioned adjacent each said thrust bar to drive said draw tube when said drive bar is cammed by said cam member; gear means connecting said motor means to said wire holding tube means for rotating said wire holding tube means; and external switch means moveably mounted on said housing, said external switch means being adapted to energize said motor causing said gear means to rotate.

2. A portable surgical wire inserting apparatus as claimed in claim 1 wherein said split collet member is threaded and the interior of said draw tube is threaded so that said split collet member is screwed into said draw tube in a predetermined position.

3. A portable surgical wire inserting apparatus as claimed in claim 2 including a lock screw means adjustably mounted in said draw tube adapted to abut said split collet member when said collet member is screwed into said draw tube, said lock screw means being adapted to be positioned in said draw tube in a manner to lock said split collet in position.

4. A portable surgical wire inserting apparatus as claimed in claim 1 including second cam means mounted to said head assembly constructed to engage the other end of each said thrust bar, pivoting said thrust bar around one of said pivot points to engage said draw tube driving means to drive said draw tube a predetermined distance.

5. A portable surgical wire inserting instrument comprising a housing, said housing defining a handle portion and a drive portion, a removable power pack slidably mounted and completely enclosed within said handle portion, a motor means mounted in said removable power pack, a removable battery pack electrically connected to said motor means and mounted in said power pack, said removable battery pack including guard means mounted thereto assuring installation of said battery pack in said power pack in only one direction, a wire holding assembly mounted in said drive portion, said wire holding assembly comprising a tube having a coned end, a draw tube slidably mounted adjacent said coned tube, a split collet adjustably mounted to said draw tube and adapted to engage the coned end of said coned tube, a first cam means slidably mounted in said drive portion defining a pivot point, thrust bar means pivotally connected to said pivot point, said first cam means being adapted to drive said draw tube rearward a predetermined distance, a second cam means having a plurality of camming sides rotatably mounted in said housing so that one of said sides engages said thrust bar means to engage and drive the thrust bar means around the pivot point against drive means connected to said draw tube so that said draw tube is slidably moved an additional distance beyond said predetermined distance, each camming side having a different configuration from the adjacent side so that said draw tube is moved to other predetermined distances beyond said predetermined distance as the second cam means is rotated depending upon which cam side engages the thrust bar means.

6. A portable surgical wire inserting instrument comprising a housing defining a handle, a head assembly and a nose piece removably mounted in the head assembly, a removable power pack mounted in said handle, a motor and a source of power electrically connected to the motor and mounted in said power pack, gear means extending from the power pack and connected by a drive shaft to the motor, a wire handling assembly mounted in said head assembly, said wire handling assembly comprising a split collet adjustably secured to a draw tube and positioned within a coned tube, said wire handling assembly being positioned within said head assembly and adapted to grip a plurality of different diameter surgical wires through cam means comprising a knob and cam mechanism located on the head assembly, rotation of the knob to one of a number of different predetermined positions cams a thrust bar means pivotally connected to said cam mechanism rearward against means extending from said draw tube moving the draw tube rearward pulling the split collet into a coned tube causing the jaws of the split collet to close, additional rearward movement of the draw tube being obtained by a second cam mechanism mounted to said handle causing the jaws of the split collet to close further and grip a surgical wire, a second gear means connected to the wire handling assembly engaging the first gear means with both gear means being adapted to rotate the coned tube upon energization of the motor.

7. A portable surgical wire inserting apparatus as claimed in claim 6 wherein said cam mechanism comprises a cam member moveably mounted adjacent a wall of a drive bar, said drive bar defining at least one pivot point on which said thrust bar means rotates.

8. A portable surgical wire inserting apparatus as claimed in claim 6 wherein said second cam mechanism is rotatably mounted to said handle, said second cam mechanism when rotated engaging said thrust bar means and pivoting said thrust bar means.

9. A portable surgical wire inserting apparatus as claimed in claim 6 including a thrust bearing assembly mounted to said nose piece to absorb thrust load.

10. A portable surgical wire inserting apparatus as claimed in claim 9 wherein said thrust bearing assembly comprises a thrust bearing, a retaining ring positioned adjacent the front race of the thrust bearing and support means bearing against the fixed rear race of the thrust bearing.

11. A portable surgical wire inserting apparatus as claimed in claim 6 including a disposable cap mounted onto the head assembly, said cap being formed with a thin membrane at one end which when pucntured by a surgical wire inserted into the head assembly forms a seal on the wire to keep foreign material from entering the head.

* * * * *